(12) United States Patent
Mayberg

(10) Patent No.: US 6,326,017 B1
(45) Date of Patent: Dec. 4, 2001

(54) METHODS FOR THE LOCALIZED DELIVERY OF AGENTS TO BLOOD VESSELS

(75) Inventor: Marc R. Mayberg, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 08/042,461

(22) Filed: Apr. 5, 1993

Related U.S. Application Data

(63) Continuation of application No. 07/780,614, filed on Oct. 23, 1991, now abandoned, which is a continuation of application No. 07/416,671, filed on Oct. 2, 1989, now abandoned.

(51) Int. Cl.$^7$ ................. A61F 13/00; A61K 9/14
(52) U.S. Cl. ............ 424/422; 424/423; 424/484; 424/486; 514/12; 514/56; 514/423; 604/890.1; 604/891.1
(58) Field of Search ............ 604/890.1, 891.1; 424/484, 486

(56) References Cited

U.S. PATENT DOCUMENTS

| | | | | |
|---|---|---|---|---|
| 3,797,485 | * | 3/1974 | Urquhart | 604/93 |
| 4,808,570 | * | 2/1989 | Michaeli | 514/2 |

OTHER PUBLICATIONS

Structural determinants of the Capacity of heparin . . . Castellot et al. J. Cellular Physiol. 120, 315–320 (1984).*
Inhibitors of angiotensin–Converting Enzyme . . . Vascular Injury. Powell et al. Science 245, 186, Jul. 1989.*
Moskowitz et al Brain Res. 212, 460, 1981.*
Okada et al Stroke 19, 1470, 1988.*
Mayberg et al Surgical Forum XXXIX p 496, 1988.*
Grant & Hackh's Chem. Dictionary, 1987, p 53.*
Howard et al., *J. Neurosurg.* 71:105–112, 1989.
Kim et al., *Archives of Pharmacal Res.* 9:193–199, 1986.
Leong et al., *J. Biomed. Mat. Res.* 19:941–955, 1985.
Mayberg et al., *Surgical Forum vol. XXXIX*, pp. 496–499, Oct. 1988.
McRae–Degueurce et al., *Neurosci. Lett.* 92:303–309, 1988.
Moskowitz et al., *Brain Res.* 212:460–465, 1981.
Okada et al., *Stroke* 19:1470–1476, 1988.

* cited by examiner

*Primary Examiner*—Gollamudi S. Kishore
(74) *Attorney, Agent, or Firm*—Seed Intellectual Property Law Group PLLC

(57) ABSTRACT

Methods for the localized delivery of agents to blood vessels are disclosed. The methods of the present invention provide advantages over existing methods for treating, diagnosing, or preventing, vascular disorders. Localized delivery of agents permits the use of agents, such as heparin, for which systemic distribution may be undesirable. Suitable agents include antithrombotic and anti-intimal proliferation agents. An agent may be delivered to a blood vessel by a carrier, such as a polymer, which is adapted to restrict the release of the agent into tissue adjacent to the blood vessel. Alternatively, after applying a carrier to a blood vessel, the carrier may be covered with a barrier adapted to restrict the release of the agent into tissue adjacent to the blood vessel. The methods of the present invention may be applied to a variety of surgical and nonsurgical clinical settings.

10 Claims, No Drawings

METHODS FOR THE LOCALIZED DELIVERY OF AGENTS TO BLOOD VESSELS

CROSS-REFERENCE TO RELATED APPLICATION

This application is a continuation of U.S. patent application Ser. No. 07/780,614, filed Oct. 23, 1991, now abandoned, which is a continuation of U.S. patent application Ser. No. 07/416,671, filed Oct. 2, 1989, now abandoned.

TECHNICAL FIELD

The present invention is generally directed toward the localized delivery of agents to blood vessels, and more specifically to the localized delivery of agents, such as heparin, for which systemic distribution may be undesirable.

BACKGROUND OF THE INVENTION

Agents useful for the treatment of, or protection against, disorders of blood vessels may present a considerable risk to a patient when administered systemically. Heparin is a representative example of such an agent.

Heparin compounds are sulfated glycosaminoglycans that inhibit coagulation at several stages in the clotting sequence. The most prominent anticoagulant effect is related to potentiation of antithrombin III. Heparin, when administered subcutaneously, intra-muscularyly, or intravenously, can provide systemic anticoagulation. However, variability in protein binding, half-life, distribution and coagulation testing procedures complicate the accurate administration of heparin, which must be undertaken in the hospital setting. Optimal anticoagulation is frequently difficult to achieve and often requires continuous infusion.

Hemorrhage is the primary complication associated with heparin anticoagulation although thrombocytopenia, hypersensitivity reactions, lipolysis, and rebound hypercoagulability occur less frequently. Hemorrhage during heparin therapy is directly related to the degree of anticoagulation and the duration of therapy. Recent surgery, thrombocytopenia, peptic ulcers, uremia, and concurrent antiplatelet agents all increase the risk of hemorrhage during systemic anticoagulation with heparin and represent relative contraindications to its use. From 5% to 33% of patients receiving full heparin anticoagulation suffer hemorrhagic complications, many of which are fatal or disabling.

Heparin, in addition to its antithrombotic effect, suppresses late smooth muscle cell proliferation in arteries after endothelial damage. Proliferation of smooth muscle cells in blood vessels ("myointimal proliferation") occurs in conditions such as atherosclerosis, hypertension and following various vascular surgical procedures. Despite the effectiveness of heparin as an anti-intimal proliferation agent when administered systemically, its use necessitates considerable risk, due to side effects such as those described above, and is frequently contraindicated after surgical procedures.

Due to the complications associated with systemic administration of agents useful for the treatment of, or protection against, vascular disorders, there is a need in the art for methods that provide for the localized delivery of such agents to blood vessel. The present invention fills this need, and further provides other related advantages.

SUMMARY OF THE INVENTION

Briefly stated, the present invention provides methods for the localized delivery of agents to a blood vessel. In one embodiment, the method comprises applying a carrier containing at least one agent to an external surface of a blood vessel and isolating the agent from adjacent tissue.

In another embodiment, the method comprises applying a carrier containing at least one agent to an external surface of a blood vessel, the carrier adapted to restrict the release of the agent into tissue adjacent to the blood vessel.

In yet another embodiment, the method comprises:

applying a carrier containing at least one agent to an external surface of a blood vessel; and covering the carrier with a barrier adapted to restrict the release of the agent into tissue adjacent to the blood vessel.

Within preferred embodiments of the methods, the agent comprises at least one antithrombotic agent and/or at least one anti-intimal proliferation agent.

These and other aspects of the present invention will become evident upon reference to the following detailed description.

DETAILED DESCRIPTION OF THE INVENTION

As noted above, the present invention discloses methods for the localized delivery of agents to a blood vessel. The methods provide advantages over existing methods for treating, diagnosing, or preventing, vascular disorders. The advantages include: (1) substantially eliminating, or at least reducing, side effects of an agent that result from its systemic administration, (2) providing high concentrations of the agent at the site of action, and (3) supplanting procedures such as continuous intravenous infusion.

A variety of vascular disorders exist for which localized delivery of an agent for therapeutic, diagnostic or prophylactic purposes is desirable. A representative example of such a vascular disorder is thrombosis, which is a major cause of death and disability and affects arteries and veins in nearly all organ systems of the body. The methods of the present invention provide, by localized delivery of antithrombotic agents, for selective local antithrombosis without systemic anticoagulation. Suitable antithrombotic agents include heparin, antiplatelet agents such as aspirin, thrombolytic agents such as tissue plasminogen activator, or combinations of two or more agents. For example, heparin may be used alone or in combination with one or more other antithrombotic agents.

The methods of the present invention may be applied to a variety of surgical and nonsurgical clinical conditions. Surgical settings include endarterectomy, large vessel and microvascular anastomosis, cerebral and systemic venous procedures, arteriovenous shunts, angioplasty, and free flaps. Nonsurgical settings include deep-vein thrombosis, cardiac valvular disease, and arterial stenosis.

Another representative example of a vascular disorder for which localized delivery of an agent is desirable is the proliferation of vascular smooth muscle cells ("myointimal proliferation"). As noted above, hyperplasia of vascular smooth muscle cells has been related to the pathogenesis of atherosclerosis, hypertension, and arterial stenosis after experimental or surgical endothelial injury. The complex interaction between circulating blood elements and components of the vessel wall determine in part the nature and degree of the arteriopathic response. Endothelial injury initiates platelet adherence and aggregation, with release of the smooth muscle cell mitogen platelet-derived growth factor (PDGF). In addition, exposure of the media to normally excluded serum components after endothelial injury may initiate smooth muscle cell proliferation and migration. Myointimal proliferation may be diminished by systemic administration of an anti-intimal proliferation agent, for example, heparin. However, as noted above, systemic administration of heparin is associated with considerable risk of hemorrhage and its use is limited in clinical settings with increased potential risk for bleeding. The methods of the present invention provide, by localized delivery of anti-intimal proliferation agents, for selective local anti-intimal proliferation effects without significant systemic effects. Suitable anti-intimal proliferation agents include heparin, calcium antagonists such as diltiazem, inhibitors of angiotensin-converting enzyme such as cilazapril, or combinations of two or more agents. For example, heparin may be used alone or in combination with one or more other anti-intimal proliferation agents.

It may be advantageous in certain situations to use the methods of the present invention to deliver two or more different types of agents. For example, one or more anti-thrombotic agents may be used in combination with one or more anti-intimal proliferation agents.

Localized delivery of an agent to a blood vessel by the methods of the present invention is achieved by applying a carrier containing at least one agent to an external ("adventitial") surface of a blood vessel and isolating the agent, or agents, from the adjacent tissue. An agent may act on a wall or the lumen of a blood vessel. The blood vessel to which an agent is applied may be an artery or a vein. A preferred blood vessel is an artery or vein undergoing anastomosis. A preferred artery is an artery undergoing endarterectomy, such as a carotid, aorta or femoral artery. The carrier may be applied to the entire circumference of a blood vessel or to a portion thereof. Similarly, the portion of the length of blood vessel to which an agent is applied will be evident to one skilled in the art depending upon the particular circumstances.

Isolation of an agent from tissue adjacent to a blood vessel may be subsequent to, or simultaneous with, the applying of a carrier containing the agent to a blood vessel. In one embodiment of a method within the present invention for simultaneously applying and isolating an agent, a carrier is used which has been adapted to restrict the release of the agent into tissue adjacent to the blood vessel. Representative examples of such a carrier include a matrix, which promotes substantially unidirectional delivery of an agent contained within, or a pump.

Polymers are one type of matrix that may be constructed to achieve unidirectional delivery of an agent. For example, a polymer may comprise two layers, one of which degrades faster than the other. The polymer is applied to a vessel such that the faster degrading layer is closer to the vessel's external surface. Alternatively, a polymer may be produced in which only one of the layers contains an agent and the other layer forms a barrier to release. Another type of suitable matrix is a sponge with a backing that forms a barrier to release. Where a pump is used as the carrier of an agent, its outlet may be adapted to form a seal with an external surface of a blood vessel and thereby restrict the release of the agent into adjacent tissue. It will be evident to one skilled in the art that other carriers may be substituted for those described herein.

In one embodiment of a method within the present invention for isolating an agent subsequent to applying it to a blood vessel, the carrier applied to the blood vessel may be covered with a barrier adapted to substantially limit the release of the agent into tissue adjacent to the blood vessel. A representative example of such a barrier is a substantially impermeable shell. Suitable materials for such a shell include a silicon polymer, e.g., Silastic (available from Dow-Corning, Midland, Mich.) or other noninflammatory materials, such as polyethylene. In a preferred embodiment, the carrier which is covered with a barrier is a polymer.

Polymers suitable for use as carriers within the methods of the present invention include a variety of chemical compositions. For example, polyvinyl alcohols, polyanhydrides and polylactids may be used. Derivatives may be produced by modification of the structure of a monomer precursor and/or by formation of a polymer from two or more different monomers to yield a copolymer. A polymer may or may not be bioerodible (biodegradable). Polyvinyl alcohol (PVA) is an example of a nonbioeodible polymer. PVA is a nontoxic, water-soluble polymer which has been used in humans for intravenous volume expansion and embolization procedures. Bioerodible polymers include polyanhydrides (such as poly[bis(p-carboxyphenoxy) propane anhydride] and poly[terephthalic acid], described in Leong et al., *J. Biomed. Mat. Res.* 19:941–955, 1985), polyanhydride sebacic acid copolymers (such as a copolymer of poly[bis(p-carboxyphenoxy) propane anhydride] and sebacic acid, described in Howard et al., *J. Neurosurg.* 71:105–112, 1989), and polylactides (such as poly[DL-lactide-co-glycolide], described in McRae-Degueurce et al., *Neurosci. Lett.* 92:303–309, 1988). Where a controlled rate of release for a desired time period is required, it will be evident to one skilled in the art to select an appropriate polymer.

The following examples are offered by way of illustration, and not by way of limitation.

EXAMPLES

Example 1

Local Anticoagulation In Carotid Artery Without Systemic Effect

Eleven male Sprague-Dawley rats weighing 350–450 gm were anesthetized with 80 mg/kg i.p. sodium pentobarbital and were mechanically ventilated through a tracheostomy. The distal common, external and internal carotid arteries were exposed bilaterally in the rat's neck through a midline incision, and a 2-French balloon embolectomy catheter was introduced into both external carotid arteries. Advancing the inflated embolectomy catheter cephalad over 1 cm proximal to the carotid bifurcation produced consistent endothelial desquamation in this segment of the artery. Additional vessel wall injury was produced by passing an 0.8-mm wire along the desquamated luminal surface. Six hundred units (0.03 ml: 20,000 units/ml) of heparin sulfate (Organon, Inc.; West Orange, N.J.) was mixed with 0.06 ml polyvinyl alcohol (PVA) (Elvax, Du Pont Corp., Wilmington, Del.; 16% wt.: vol. in water) to produce a viscous gel. Immediately after mixing, the heparin/PVA gel was applied around the adventitial surface of the de-endothelialized distal left (treated) common carotid artery and surrounded by a Silastic (Dow-Corning, Midland, Mich.) shell to prevent release into adjacent tissues, PVA without heparin (0.09 ml) was similarly applied to the right (control) common carotid artery.

Thirty minutes after application of the PVA, both common carotid arteries were occluded by microclips at the proximal and distal ends of the segment with injured endothelium. After 1 hour of occlusion, the systemic prothrombin time (PT) and partial thromboplastin time (PTT) were determined from arterial blood drawn from a femoral catheter. The microclips were then removed, and blood flow was established again in both carotid arteries for 5 minutes. Vessels were perfusion-fixed in situ at physiologic pressure (mean 80 mm Hg) with intracardiac 0.12 M phosphate buffer (pH 7.4) followed by 4% paraformaldehyde and 1% glutaraldehyde in buffer. The common carotid arteries were removed and placed in 1.5% glutaraldehyde/buffer overnight.

One pair of carotid arteries for scanning electron microscopy (SEM) was placed in buffered 1% osmium tetroxide, dehydrated in graded ethanols, and critical-point dried. The luminal surface was exposed after mounting, coated with gold, examined, and photographed with a JEOL scanning electron microscope (Peabody, Mass.).

For light microscopy, the remaining 10 pairs of vessels were embedded in ethyl methacrylate (JB-4, Sorvall, Wilmington, Del.), sectioned at 3 $\mu$m thicknesses, mounted on glass slides, and stained with hematoxylin and eosin. Cross-sectional areas for intraluminal thrombus, vessel wall, and lumen were determined from 10 adjacent sections at the site of maximal thrombosis for each vessel using an automated image analysis system (Bioquant System IV, Nashville, Tenn.). Thrombus size was expressed as the percentage ratio of the cross-sectional area of thrombus to lumen, and treated and control vessels were compared statistically using Student's paired two-tailedt test.

Additional experiments were performed to evaluate the systemic distribution of heparin from PVA after endothelial injury only (no carotid occlusion). A group of eight rats underwent balloon catheter endothelial desquamation and application of PVA as above, but the vessels were not occluded. In this model, there was no significant thrombosis in treated or control arteries. Systemic PT and PTT for these eight unoccluded rats were determined 60 minutes after application of PVA.

PT and PTT were also determined in a third group of five untreated rats receiving balloon catheter endothelial desquamation without application of heparin/PVA.

Table 1 shows PT and PTT for nine rats undergoing endothelial injury with temporary occlusion and heparin/PVA treatment, the eight unoccluded rats undergoing endothelial injury and heparin/PVA treatment, and the five untreated rats undergoing endothelial injury only. There is no significant difference in PT or PTT between the two treated groups (with or without temporary occlusion) and the untreated group after endothelial injury.

TABLE 1

Coagulation Parameters in Rats After Application of Heparin in Polyvinyl Alcohol Polymer to Common Carotid Artery

| Group | n | Prothrombin time(sec) | Partial thromboplastin time(sec) |
|---|---|---|---|
| Endothelial injury with temporary occlusion + heparin | 9 | 12.2 ± 1.2 | 22.0 ± 0 |
| Endothelial injury + heparin | 8 | 12.4 ± 0.6 | 21.7 ± 2.2 |
| Endothelial injury only | 5 | 11.8 ± 0.8 | 22.0 ± 0 |

Data are mean ± SD

SEM of the luminal surface of control and heparin/PVA-treated desquamated rat common carotid arteries were performed. The control vessel showed an extensive thrombus composed primarily of erythrocytes in a dense fibrin network that completely occludes the lumen. The treated vessel, on the other hand, demonstrated complete endothelial desquamation with exposed subendothelial collagen. The luminal surface of the treated vessel was coated with a monolayer of adherent platelets, but no fibrin formation or erythrocyte thrombus was present.

In light microscopic sections, severe endothelial injury was seen in control and treated vessels, with frequent disruption of the elastica and occasional damage to the media. At regions of endothelial injury without thrombus in either class of vessel, there was a sparse monolayer of platelets and leukocytes adherent to the underlying vessel wall. Intraluminal thrombus was composed of erythrocytes associated with abundant fibrin strands. Except for occasional localized disruptions of the medial architecture, there were no alterations in smooth muscle cell morphology or vessel wall thickness in either class of vessel. In control vessels, thrombus formation was more extensive in those with more pronounced damage to the media. Inflammatory changes related to PVA application were not observed in either class of vessel.

Table 2 shows the distribution of thrombus formation for control and treated vessels, expressed as the thrombus: lumen ratio. A significant (>20%) intraluminal thrombus was present in all 10 control vessels, four of which were completely occluded. In contrast, significant thrombus was visible in only one of 10 treated vessels.

TABLE 2

Distribution of Thrombus: Lumen Ratios in Rat Common Carotid Arteries Treated With Polyvinyl Alcohol Polymer or Polymer Containing Heparin After Endothelial Damage and 1-Hour Occlusion

| Thrombus/lumen ratio (%) | Control (polymer only) | Treated (heparin/polymer) |
|---|---|---|
| 0–10 | 0 | 9 |
| 20–40 | 3 | 1 |
| 40–60 | 2 | 0 |
| 60–80 | 2 | 0 |
| 80–100 | 3 | 0 |
| Mean ± SD | 60.2 ± 25.8% | 4.1 ± 9.6% |

The average cross-sectional area for intraluminal thrombus, vessel wall, and lumen for control and treated vessels were compared. Thrombus area was reduced from 251±119 $\mu m^3$ in control vessels to 15±36 $\mu m^3$ in treated vessels (p<0.005) although there were no significant differences in vessel wall or lumen area between classes of vessels. The reduction in intraluminal thrombus formation is reflected in the thrombus: lumen ratio, which was reduced from 60.2±25.8% in control vessels to 4.1±9.6% (p<0.005) in treated vessels (Table 2).

Example 2

Local Anti-Intimal Proliferation Effect Without Systemic Anticoagulation

Thirty adult male Sprague-Dawley rats weighing 450–500 gm were anesthetized with sodium pentobarbital (50 mg/kg intraperitoneally) after the administration of atropine sulfate (0.05 mg/kg intramuscularly). The left common, external and internal carotid arteries were exposed in the neck through a midline incision, and a 2-French balloon embolectomy catheter introduced into the external carotid artery. The catheter was positioned in the proximal common carotid artery (CCA), then inflated and withdrawn three times to produce a consistent 2 cm segment of endothelial desquamation. Four hundred units (0.02 ml, 20,000 μ/ml) of heparin sulfate (Organon, Inc.; West Orange, N.J.) was mixed with 0.04 ml of polyvinyl alcohol (PVA) (Elvanol, Du Pont Corp., Wilmington, Del.; 16% weight: volume in water) to produce a viscous gel. Using sterile technique, the heparin/PVA gel was applied immediately after mixing to the adventitial surface of the de-endothelialized CCA, and surrounded by a silastic shell to prevent release into adjacent tissue. In control rats, PVA without heparin (0.06 ml) was similarly applied to the de-endothelialized left CCA. Animals in both groups were sacrificed at 5 (N=10), 10 (N=10) and 20 (N=10) days after endothelial injury by perfusion-fixation at physiologic pressure (mean 80 mmHg) with 100 ml intracardiac 0.12 M phosphate buffer (PB;pH 7.4) followed by 200 ml of 4% paraformaldehyde and 1% glutaraldehyde in PB. Fifteen minutes before sacrifice, Evans blue dye (Sigma, St. Louis; 60 mg/kg in phosphate buffered saline, pH 7.4) was injected via a left femoral catheter. In animals from groups at 5 and 10 days after endothelial injury, 2.7 ml of femoral venous blood was collected prior to sacrifice for systemic prothrombin time (PT) and partial thromboplastin time (PTT). Additionally, animals in the 5 day group had PT and PTT determinations from femoral venous samples drawn at 1 day after injury.

After perfusion-fixation, 10 mm segments of left CCA were removed, placed in 1.5% glutaraldehyde/PB overnight, then divided into two 5 mm segments for light microscopy/immunohistochemistry and scanning electron microscopy (SEM), respectively. The distal 5 mm segment of the CCA for SEM was placed in buffered 1% osmium tetroxide, dehydrated in graded ethanols, and critical-point dried. The luminal surface was exposed after mounting, coated with gold, and examined and photographed with a JEOL scanning electron microscope (Peabody, Mass.).

For light microscopy, the proximal 5 mm segment of vessel was embedded in ethylmethacrylate (JB-4, Sorvall, Wilmington, Del.), sectioned at 3 μm thickness, mounted on glass slides, and stained with hematoxylin and eosin. Cross-sectional areas for lumen, intima, and media were determined from 10 adjacent sections using an automated image analysis system (Bioquant System IV, Nashville, Tenn.). Grouped data for morphometric indices from treated and control vessels were compared at each period using Student's two-tailedt test.

From each specimen, four adjacent sections at 3 μm thickness from the proximal CCA segment in JB-4 were prepared for immunohistochemistry with monoclonal antibodies (Ab) directed against human myocardial actin. Briefly, mounted sections were incubated with 1% bovine serum albumin in phosphate-buffered saline (1% BSA-PBS) for 30 minutes at 37° C. to block non-specific binding of Ab to protein. Sections were then incubated at 37° C. with 1:500 primary Ab (monoclonal-HHF mouse anti-actin) (44,45) for 90 minutes, 1:500 secondary Ab (rabbit anti-mouse IgG; ICM Immunobiologicals, Lyle, Ill.) for 30 minutes, then 1:25 tertiary Ab (goat anti-rabbit IgG conjugated to 5 nm colloidal gold, Janssen Life Sciences Products, Olen, Belgium) for 15 minutes. The sections were reacted with silver nitrate solution to enhance particulate size, so that each AB-conjugated gold particle was visible by both light and electron microscopy.

Table 3 shows PT and PTT determinations for PVA/heparin-treated and control (PVA only) rats at 1, 5 and 10 days after application of polymer. There was no significant difference in either coagulation parameter between treated and control groups at each time period.

TABLE 3

Systemic Coagulation Parameters in Rats After Application of Heparin in Polyvinyl Alcohol (PVA) to Common Carotid Artery

| Treatment | Time after application of polymer | N | Prothrombin time(sec) | Partial thromboplastin time(sec) |
|---|---|---|---|---|
| PVA/Heparin | 1 day | 4 | 13.0 ± 2.9 | 19.3 ± 3.7 |
| PVA only | | 5 | 11.8 ± 0.8 | 21.0 ± 2.3 |
| PVA/Heparin | 5 days | 5 | 11.5 ± 0.5 | 15.4 ± 4.6 |
| PVA only | | 5 | 11.6 ± 0.3 | 15.8 ± 3.6 |
| PVA/Heparin | 10 days | 5 | 11.7 ± 0.4 | 17.7 ± 4.7 |
| PVA only | | 5 | 11.3 ± 0.7 | 18.4 ± 3.3 |

Data are mean ± SD

The adequacy of balloon catheter endothelial desquamation and the degree of endothelial regeneration were assessed by direct observation of Evans blue deposition on the exposed subendothelial surface at sacrifice. At 5 days after injury in both groups, the blue-stained region of the luminal surface occupied the entire segment of injured CCA. Progressively at 10 and 20 days after endothelial injury, there was evidence of endothelial regeneration at either margin of intact endothelium, which was limited to approximately 3.5 mm at 20 days in both treated and control vessels.

At 5 days after injury, light microscopic sections of control vessels showed a monolayer of platelets adherent to the denuded subendothelium, except in those regions in which a thin layer of proliferating SMC was present on the luminal aspect of the internal elastic lamina. In treated vessels at 5 days, the entire luminal surface was covered with a monolayer of platelets without evidence of myointimal proliferation. At 10 days, control vessels uniformly showed significant myointimal proliferation, which covered the denuded surface completely and slightly narrowed luminal diameter. In heparin/PVA-treated vessels at 10 days, a less prominent layer of proliferating SMC incompletely covered the luminal surface, with a monolayer of platelets present over the remaining lumen. At 20 days the intimal thickening was more pronounced in control vessels, with a marked reduction in lumen by the proliferating SMC, compared to only moderate intimal proliferation with a slight reduction in lumen in treated vessels. Inflammatory changes related to the polymer application were minimal in both treated and control specimens at each time period.

Cross-sectional areas of media, intima, and lumen for control and heparin/PVA-treated CCA at 5, 10 and 20 days after endothelial injury were compared. Intimal cross-sectional area was significantly less in treated vessels compared to controls at 5 days (0±0.0 $mm_2$ vs. 0.014±0.008 $mm_2$; $p<0.005$), 10 days (0.052±0.012 $mm_2$ vs. 0.119±0.016 $mm_2$; $p<0.005$) and 20 days (0.095±0.057 $mm_2$ vs. 0.210±0.055 $mm_2$; $p<0.025$). Intimal SMC proliferation was reflected in significant reduction in luminal cross-sectional area for control CCA compared to treated vessels at 20 days ($p<0.05$). There was no change in cross-sectional area of the media at any time point in either treated or control vessels.

SEN of the de-endothelialized CCA showed no differences in the luminal surface between control and treated vessels. In all specimens, normal endothelium at the margin of the denuded segment was characterized by ovoid cells with distinct cell margins oriented in the longitudinal axis of the vessel. Regenerating endothelial cells could not be differentiated from adjacent pre-existing cells. The denuded luminal surface was completely devoid of endothelium and was covered by a sparse monolayer of platelets.

In sections reacted for anti-actin immunohistochemistry, Ab conjugated to silver-enhanced colloidal gold were visible as black particulate staining in the cytoplasm of SMC and proliferating myointimal cells. Staining density in both control and treated vessels was less in myointimal cells compared to medial SMC. The increase in intimal cross-sectional area over time in control compared to heparin/PVA-treated vessels was reflected in similar differences for actin-positive cells in the intima.

From the foregoing, it will be evident that, although specific embodiments of the invention have been described herein for purposes of illustration, various modifications may be made without deviating from the spirit and scope of the invention.

What is claimed is:

1. A method for the treatment of vascular disorders, comprising:

exposing an external surface of an artery or vein;

applying a polymer matrix, which is permeable to an agent for the treatment of a vascular disorder and is impregnated with said agent, directly to said external surface; and covering said polymer matrix with a barrier adapted to restrict the release of said agent into tissue adjacent to said artery or vein, so that said agent diffuses from said polymer directly to said external surface of said artery or vein, thereby producing a localized effect on said artery or vein without systemic effect.

2. A method for the treatment of vascular disorders, comprising applying a polymer matrix, which is permeable to an agent for the treatment of a vascular disorder and is impregnated with said agent, directly into contact with an external surface of an artery or vein, said polymer matrix covered with a barrier adapted to restrict the release of said agent into tissue adjacent to said artery or vein so that said agent diffuses from said polymer directly to said external surface of said artery or vein, thereby producing a localized effect on said artery or vein without systemic effect.

3. A method for the treatment of vascular disorders, comprising:

applying a polymer matrix, which is permeable to an agent for the treatment of a vascular disorder and is impregnated with said agent, directly into contact with an external surface of an artery or vein; and covering said polymer matrix with a barrier adapted to restrict the release of said agent into tissue adjacent to said artery or vein, so that said agent diffuses from said polymer directly to said external surface of said artery or vein, thereby producing a localized effect on said artery or vein without systemic effect.

4. The method of any of claims 1, 2, and 3 wherein said artery or vein is an artery.

5. The method of claim 4 wherein said artery is a carotid, aorta or femoral artery.

6. The method of any of claims 1, 2, and 3 wherein said artery or vein is a vein.

7. The method of any of claims 1, 2, and 3 wherein said agent comprises at least one antithrombotic agent selected from the group consisting of aspirin, heparin and tissue plasminogen activator.

8. The method of any of claims 1, 2 and 3 wherein said agent comprises at least one anti-intimal proliferation agent selected from the group consisting of diltiazem, heparin and cilazapril.

9. The method of claim 1 or claim 3 wherein said step of covering comprises substantially surrounding the external surface, to which a polymer matrix has been applied, with a shell impermeable to said agent.

10. The method of claim 9 wherein said impermeable shell comprises a silicon polymer.

* * * * *